(12) United States Patent
Dong et al.

(10) Patent No.: US 11,028,110 B2
(45) Date of Patent: Jun. 8, 2021

(54) PROCESS FOR THE ALKOXYCARBONYLATION OF ALCOHOLS

(71) Applicant: EVONIK DEGUSSA GMBH, Essen (DE)

(72) Inventors: Kaiwu Dong, Bo Zhou (CN); Ralf Jackstell, Cuxhaven Altenwalde (DE); Helfried Neumann, Rostock (DE); Matthias Beller, Ostseebad Nienhagen (DE); Dirk Fridag, Haltern am See (DE); Dieter Hess, Marl (DE); Katrin Marie Dyballa, Recklinghausen (DE); Frank Geilen, Haltern am See (DE); Robert Franke, Marl (DE)

(73) Assignee: EVONIK OPERATIONS GMBH, Essen (DE)

( * ) Notice: Subject to any disclaimer, the term of this patent is extended or adjusted under 35 U.S.C. 154(b) by 79 days.

(21) Appl. No.: 15/649,770

(22) Filed: Jul. 14, 2017

(65) Prior Publication Data

US 2018/0022765 A1 Jan. 25, 2018

(30) Foreign Application Priority Data

Jul. 19, 2016 (EP) .................................. 16180052

(51) Int. Cl.
| C07F 9/50 | (2006.01) |
| C07C 67/36 | (2006.01) |
| C07C 67/38 | (2006.01) |
| C07D 471/00 | (2006.01) |
| C07F 15/00 | (2006.01) |

(52) U.S. Cl.
CPC ............ C07F 9/5045 (2013.01); C07C 67/36 (2013.01); C07C 67/38 (2013.01); C07D 471/00 (2013.01); C07F 15/0066 (2013.01)

(58) Field of Classification Search
None
See application file for complete search history.

(56) References Cited

U.S. PATENT DOCUMENTS

| 8,969,560 | B2 | 3/2015 | Eastham et al. |
| 9,381,503 | B2 | 7/2016 | Eastham et al. |
| 2011/0065950 | A1* | 3/2011 | Riisager ............... B01J 31/0222 560/129 |
| 2017/0022137 | A1 | 1/2017 | Dong et al. |
| 2017/0022138 | A1 | 1/2017 | Dong et al. |
| 2017/0022139 | A1 | 1/2017 | Dong et al. |
| 2017/0022234 | A1 | 1/2017 | Jennerjahn et al. |
| 2017/0022235 | A1 | 1/2017 | Dong et al. |
| 2017/0022236 | A1 | 1/2017 | Dong et al. |

FOREIGN PATENT DOCUMENTS

| EP | 0662467 A1 | 7/1995 |
| JP | 2013-516449 A | 5/2013 |

(Continued)

OTHER PUBLICATIONS

Zhou et al. (J. Molecular Catalysis A: Chemical 116(1997), 329-333 (Year: 1997).*

(Continued)

*Primary Examiner* — Yun Qian
(74) *Attorney, Agent, or Firm* — Smith, Gambrell & Russell, LLP

(57) ABSTRACT

The invention relates to a process comprising the following process steps:
a) introducing a first alcohol, the first alcohol having 2 to 30 carbon atoms;
b) adding a phosphine ligand and a compound which comprises Pd, or adding a complex comprising Pd and a phosphine ligand;
c) adding a second alcohol;
d) supplying CO;
e) heating the reaction mixture, the first alcohol reacting with CO and the second alcohol to form an ester;
where the phosphine ligand is a compound of formula (I)

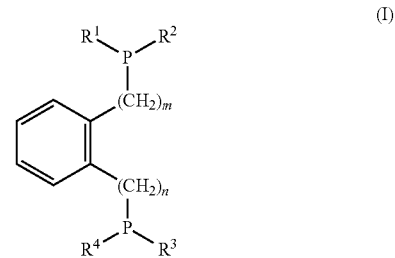

where
m and n are each independently 0 or 1;
$R^1$, $R^2$, $R^3$, $R^4$ are each independently selected from —($C_1$-$C_{12}$)-alkyl, —($C_3$-$C_{12}$)-cycloalkyl, —($C_3$-$C_{12}$)-heterocycloalkyl, —($C_6$-$C_{20}$)-aryl, —($C_3$-$C_{20}$)-heteroaryl;
at least one of the $R^1$, $R^2$, $R^3$, $R^4$ radicals is a —($C_3$-$C_{20}$)-heteroaryl radical;
and
$R^1$, $R^2$, $R^3$, $R^4$, if they are —($C_1$-$C_{12}$)-alkyl, —($C_3$-$C_{12}$)-cycloalkyl, —($C_3$-$C_{12}$)-heterocycloalkyl, —($C_6$-$C_{20}$)-aryl or —($C_3$-$C_{20}$)-heteroaryl,
may each independently be substituted by one or more substituents selected from —($C_1$-$C_{12}$)-alkyl, —($C_3$-$C_{12}$)-cycloalkyl, —($C_3$-$C_{12}$)-heterocycloalkyl, —O—($C_1$-$C_{12}$)-alkyl, —O—($C_1$-$C_{12}$)-alkyl-($C_6$-$C_{20}$)-aryl, —O—($C_3$-$C_{12}$)-cycloalkyl, —S—($C_1$-$C_{12}$)-alkyl, —S—($C_3$-$C_{12}$)-cycloalkyl, —COO—($C_1$-$C_{12}$)-alkyl, —COO—($C_3$-$C_{12}$)-cycloalkyl, —CONH—($C_1$-$C_{12}$)-alkyl, —CONH—($C_3$-$C_{12}$)-cycloalkyl, —CO—($C_1$-$C_{12}$)-alkyl, —CO—($C_3$-$C_{12}$)-cycloalkyl, —N—[($C_1$-$C_{12}$)-alkyl]$_2$, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, —($C_3$-$C_{20}$)-heteroaryl, —($C_3$-$C_{20}$)-heteroaryl-($C_1$-$C_{12}$)-alkyl, —($C_3$-$C_{20}$)-heteroaryl-O—($C_1$-$C_{12}$)-alkyl, —COOH, —OH, —SO$_3$H, —NH$_2$, halogen.

15 Claims, No Drawings

(56) References Cited

FOREIGN PATENT DOCUMENTS

| WO | 2011/083305 A1 | 7/2011 |
|---|---|---|
| WO | 2012/131027 A1 | 10/2012 |

OTHER PUBLICATIONS

Canadian Office Action dated Oct. 15, 2018 for CA Patent Application No. 2,973,454 (3 pages).
Japanese Office Action dated Oct. 16, 2018 for JP Patent Application No. 2017-137956 (3 pages in Japanese with English machine translation).
Zhou, H., et al. Catalytic carbonylation of α-(6-methoxyl-2-naphthyl)ethanol to methyl esters of naproxen using $PdCl_2$-$CuCl_2$-$PPh_3$-acid catalyst system. Journal of Organometallic Chemistry. 1998. vol. 556. pp. 239-242.
Singapore Search Report for SG 10201705855W, dated Feb. 22, 2018 (3 pages).
Liu, Qiang, et al. Domino Catalysis: Palladium-Catalyzed Carbonylation of Allylic Alcohols to β, γ-Unsaturated Esters. Angewandte Chemie International Edition, 2013, 52, pp. 8064-8068.
Liu, Qiang, et al. Supporting Information for Domino Catalysis: Palladium-Catalyzed Carbonylation of Allylic Alcohols to β, γ-Unsaturated Esters. Angewandte Chemie International, 2013 (38 pages).
Dong, K. et al. Palladium-Catalyzed Carbonylation of sec- and tert-Alcohols. Angewandte Chemie International, 2017, 56, pp. 6203-6207.
Dong, K. et al. Supporting Information for Palladium-Catalyzed Carbonylation of sec- and tert-Alcohols. Angewandte Chemie International, 2017 (54 pages).
U.S. Appl. No. 15/649,743, filed Jul. 14, 2017, Dong et al.
U.S. Appl. No. 15/649,759, filed Jul. 14, 2017, Dong, et al.
U.S. Appl. No. 15/649,781, filed Jul. 14, 2017, Dong, et al.
U.S. Appl. No. 15/651,042, filed Jul. 17, 2017, Fang, et al.
U.S. Appl. No. 15/651,105, filed Jul. 17, 2017, Dong, et al.
U.S. Appl. No. 15/651,169, filed Jul. 17, 2017, Dong, et al.
U.S. Appl. No. 15/651,062, filed Jul. 17, 2017, Dong, et al.
European Search Report dated Dec. 19, 2016 for EP 16 18 0052 (1 page).
Zhou, H, et al. Catalytic carbonylation of α-(6-methoxyl 2-naphthyl to methyl esters of naproxen using $PdCl_2$-$CuCl_2$-$PPh_3$-Acid catalyst system. Journal of Organometallic Chemistry, No. 556, 1998, pp. 239-242.
Clegg, William, et al. Highly active and selective catalysts for the production of methyl propanoate via the methoxycarbonylation of ethane. Chem. Commun. 1999, pp. 1877-1878.
Armarego, Wilfred L.F., et al. Purification of Laboratory Chemicals, Butterworth Heinemann (Elsevier), 6th edition, Oxford 2009 (index and chapter abstracts provided).
Harris, Robin K. et al. NMR Nomenclature, Nuclear Spin Properties and Conventions for Chemical Shifts. Pure Appl. Chem., 2001, No. 73, pp. 1795-1818.
Harris, Robin K. et al. Further Conventions for NMR Shielding and Chemical Shifts. Pure Appl. Chem., 2008, No. 80, pp. 59-84.
Köppe, Ralf, et al. Quntenchemische und Experimentelle Untersuchungen zur Stabilität und Struktur von $GaAs_5$ und $InAs_5$:Angew. Chem. 2004, No. 116, 2222-2225.
Budzelaar, Peter H.M. et al. Synthesis and Coordination Chemistry of a New Class of Binucleating Ligands: Pyridyl-Substituted Diphosphines. Organometallics 1990, No. 9, 1222-1227.
Examination Search Report dated Oct. 7, 2019 for Canadian Patent App No. 2,973,454 (3 pages).
Examination Report of the Patent office of the Cooperation Council for the Arab States of the Gulf dated Jul. 4, 2019 for Patent App No. GC 2017-33715 (4 pages).
Translation of Chinese Office Action for Patent App No. 201710584323.3 (7 pages).
Translation of Chinese First Office Action dated Feb. 3, 2020 for Patent App No. 201710584323.3 (4 pages).
Translation of Chinese Search Report for Patent App No. 201710584323.3 (2 pages).
Second Office Action received in Chinese Patent Application No. 201710584323.3 dated Jul. 23, 2020. (7 pages in Chinese with English translation).
Canadian Office Action dated Jun. 25, 2019 for CA Patent Application No. 2,973,454 (3 pages).
Translation of Mexican Office Action dated Jul. 23, 2021 for Mexican Patent Application No. MX/a/2017/009228 (3 pages).

\* cited by examiner

PROCESS FOR THE ALKOXYCARBONYLATION OF ALCOHOLS

The present invention relates to a novel process for the alkoxycarbonylation of alcohols.

The alkoxycarbonylation of ethylenically unsaturated compounds is a known process for preparing esters. This method is used to react ethylenically unsaturated compounds (olefins) with carbon monoxide and alcohols in the presence of a metal-ligand complex to give the corresponding esters. Typically, the metal used is palladium. The following scheme shows the general reaction equation of an alkoxycarbonylation:

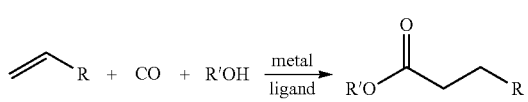

A very good catalytic system for this process was developed by Lucite-now Mitsubishi Rayon—and uses a ligand based on 1,2-bis(di-tert-butylphosphinomethyl)benzene (DTBPMB) (W. Clegg, G. R. Eastham, M. R. J. Elsegood, R. P. Tooze, X. L. Wang, K. Whiston, Chem. Commun. 1999, 1877-1878).

The possibility of using compounds other than ethylenically unsaturated compounds and reacting them with alcohols and CO to give the corresponding esters, in the form of an alkoxycarbonylation reaction, is hitherto unknown.

Against this background, the problem addressed by the present invention is that of providing an alkoxycarbonylation process for the preparation of esters, which uses raw materials other than ethylenically unsaturated compounds as a starting product. Of particular interest here is the use of alcohols as a starting product for the alkoxycarbonylation.

It has surprisingly emerged that this problem is solved by an alkoxycarbonylation process wherein particular benzene-based diphosphine ligands are used, in which at least one phosphine group is substituted by a heteroaryl radical. The process of the invention is notable for high yields, based on the alcohols used as reactants.

The invention therefore relates to a process comprising the following process steps:
a) introducing a first alcohol, the first alcohol having 2 to 30 carbon atoms;
b) adding a phosphine ligand and a compound which comprises Pd, or adding a complex comprising Pd and a phosphine ligand;
c) adding a second alcohol;
d) supplying CO;
e) heating the reaction mixture, the first alcohol reacting with CO and the second alcohol to form an ester;
where the phosphine ligand is a compound of formula (I)

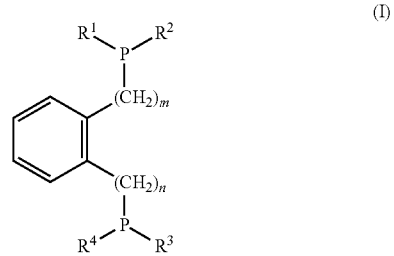

where
m and n are each independently 0 or 1;
$R^1$, $R^2$, $R^3$, $R^4$ are each independently selected from —$(C_1-C_{12})$-alkyl, —$(C_3-C_{12})$-cycloalkyl, —$(C_3-C_{12})$-heterocycloalkyl, —$(C_6-C_{20})$-aryl, —$(C_3-C_{20})$-heteroaryl;
at least one of the $R^1$, $R^2$, $R^3$, $R^4$ radicals is a —$(C_3-C_{20})$-heteroaryl radical;
and
$R^1$, $R^2$, $R^3$, $R^4$, if they are —$(C_1-C_{12})$-alkyl, —$(C_3-C_{12})$-cycloalkyl, —$(C_3-C_{12})$-heterocycloalkyl, —$(C_6-C_{20})$-aryl or —$(C_3-C_{20})$-heteroaryl,
may each independently be substituted by one or more substituents selected from —$(C_1-C_{12})$-alkyl, —$(C_3-C_{12})$-cycloalkyl, —$(C_3-C_{12})$-heterocycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —S—$(C_1-C_{12})$-alkyl, —S—$(C_3-C_{12})$-cycloalkyl, —COO—$(C_1-C_{12})$-alkyl, —COO—$(C_3-C_{12})$-cycloalkyl, —CONH—$(C_1-C_{12})$-alkyl, —CONH—$(C_3-C_{12})$-cycloalkyl, —CO—$(C_1-C_{12})$-alkyl, —CO—$(C_3-C_{12})$-cycloalkyl, —N—$[(C_1-C_{12})$-alkyl$]_2$, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl, —COOH, —OH, —$SO_3H$, —$NH_2$, halogen.

The first and second alcohols may be identical or different, but preferably the first and second alcohols are different. In one embodiment, the first alcohol is a secondary or tertiary alcohol and the second alcohol is a primary alcohol.

In this process, process steps a), b), c) and d) can be effected in any desired sequence. Typically, however, the addition of CO is effected after the co-reactants have been initially charged in steps a) to c). Steps d) and e) can be effected simultaneously or successively. In addition, CO can also be fed in in two or more steps, in such a way that, for example, a portion of the CO is first fed in, then the mixture is heated, and then a further portion of the CO is fed in.

In one embodiment, the phosphine ligands according to the invention are compounds of one of the formulae (II) and (III)

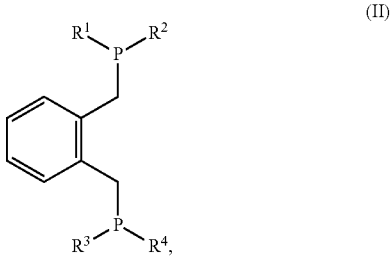

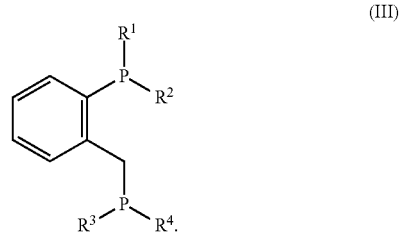

In these formulae, the $R^1$, $R^2$, $R^3$, $R^4$ radicals are each as defined above.

In one particularly preferred embodiment, the phosphine ligand according to the invention is a compound of the formula (II) where the radicals $R^1$, $R^2$, $R^3$ and $R^4$ are as defined above.

The expression $(C_1-C_{12})$-alkyl encompasses straight-chain and branched alkyl groups having 1 to 12 carbon atoms. These are preferably $(C_1-C_8)$-alkyl groups, more preferably $(C_1-C_6)$-alkyl, most preferably $(C_1-C_4)$-alkyl.

Suitable $(C_1-C_{12})$-alkyl groups are especially methyl, ethyl, propyl, isopropyl, n-butyl, iso-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethlbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The elucidations relating to the expression $(C_1-C_{12})$-alkyl also apply particularly to the alkyl groups in —O—$(C_1-C_{12})$-alkyl, —S—$(C_1-C_{12})$-alkyl, —COO—$(C_1-C_{12})$-alkyl, —CONH—$(C_1-C_{12})$-alkyl, —CO—$(C_1-C_{12})$-alkyl and —N—$[(C_1-C_{12})$-alkyl$]_2$.

The expression $(C_3-C_{12})$-cycloalkyl encompasses mono-, bi- or tricyclic hydrocarbyl groups having 3 to 12 carbon atoms. Preferably, these groups are $(C_5-C_{12})$-cycloalkyl.

The $(C_3-C_{12})$-cycloalkyl groups have preferably 3 to 8, more preferably 5 or 6, ring atoms, Suitable $(C_3-C_{12})$-cycloalkyl groups are especially cyclopropyl, cyclobutyl, cyclopentyl, cyclohexyl, cycloheptyl, cyclooctyl, cyclododecyl, cyclopentadecyl, norbornyl, adamantyl.

The elucidations relating to the expression $(C_3-C_{12})$-cycloalkyl also apply particularly to the cycloalkyl groups in —O—$(C_3-C_{12})$-cycloalkyl, —S—$(C_3-C_{12})$-cycloalkyl, —COO—$(C_3-C_{12})$-cycloalkyl, —CONH—$(C_3-C_{12})$-cycloalkyl, —CO—$(C_3-C_{12})$-cycloalkyl.

The expression $(C_3-C_{12})$-heterocycloalkyl encompasses nonaromatic, saturated or partly unsaturated cycloaliphatic groups having 3 to 12 carbon atoms, where one or more of the ring carbon atoms are replaced by heteroatoms. The $(C_3-C_{12})$-heterocycloalkyl groups have preferably 3 to 8, more preferably 5 or 6, ring atoms and are optionally substituted by aliphatic side chains. In the heterocycloalkyl groups, as opposed to the cycloalkyl groups, one or more of the ring carbon atoms are replaced by heteroatoms or heteroatom-containing groups. The heteroatoms or the heteroatom-containing groups are preferably selected from O, S, N, N(=O), C(=O), S(=O). A $(C_3-C_{12})$-heterocycloalkyl group in the context of this invention is thus also ethylene oxide.

Suitable $(C_3-C_{12})$-heterocycloalkyl groups are especially tetrahydrothiophenyl, tetrahydrofuryl, tetrahydropyranyl and dioxanyl.

The expression $(C_6-C_{20})$-aryl encompasses mono- or polycyclic aromatic hydrocarbyl radicals having 6 to 20 carbon atoms. These are preferably $(C_6-C_{14})$-aryl, more preferably $(C_6-C_{10})$-aryl.

Suitable $(C_6-C_{20})$-aryl groups are especially phenyl, naphthyl, indenyl, fluorenyl, anthracenyl, phenanthrenyl, naphthacenyl, chrysenyl, pyrenyl, coronenyl. Preferred $(C_6-C_{20})$-aryl groups are phenyl, naphthyl and anthracenyl.

The expression $(C_3-C_{20})$-heteroaryl encompasses mono- or polycyclic aromatic hydrocarbyl radicals having 3 to 20 carbon atoms, where one or more of the carbon atoms are replaced by heteroatoms. Preferred heteroatoms are N, O and S. The $(C_3-C_{20})$-heteroaryl groups have 3 to 20, preferably 6 to 14 and more preferably 6 to 10 ring atoms.

Suitable $(C_3-C_{20})$-heteroaryl groups are especially furyl, thienyl, pyrrolyl, oxazolyl, isoxazolyl, thiazolyl, isothiazolyl, imidazolyl, pyrazolyl, furazanyl, tetrazolyl, pyridyl, pyridazinyl, pyrimidyl, pyrazinyl, benzofuranyl, indolyl, isoindolyl, benzimidazolyl, quinolyl, isoquinolyl.

The expression halogen especially encompasses fluorine, chlorine, bromine and iodine. Particular preference is given to fluorine and chlorine.

In one embodiment, the $R^1$, $R^2$, $R^3$, $R^4$ radicals, if they are —$(C_1-C_{12})$-alkyl, —$(C_3-C_{12})$-cycloalkyl, —$(C_3-C_{12})$-heterocycloalkyl, —$(C_6-C_{20})$-aryl, or —$(C_3-C_{20})$-heteroaryl, may each independently be substituted by one or more substituents selected from —$(C_1-C_{12})$-alkyl, —$(C_3-C_{12})$-cycloalkyl, —$(C_3-C_{12})$-heterocycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —S—$(C_1-C_{12})$-alkyl, —S—$(C_3-C_{12})$-cycloalkyl, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl, —COOH, —OH, —SO$_3$H, —NH$_2$, halogen.

In one embodiment, the $R^1$, $R^2$, $R^3$, $R^4$ radicals, if they are —$(C_1-C_{12})$-alkyl, —$(C_3-C_{12})$-cycloalkyl, —$(C_3-C_{12})$-heterocycloalkyl, —$(C_6-C_{20})$-aryl, or —$(C_3-C_{20})$-heteroaryl, may each independently be substituted by one or more substituents selected from —$(C_1-C_{12})$-alkyl, —$(C_3-C_{12})$-cycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_2)$-alkyl.

In one embodiment, the $R^1$, $R^2$, $R^3$, $R^4$ radicals, if they are —$(C_1-C_{12})$-alkyl, —$(C_3-C_{12})$-cycloalkyl, —$(C_3-C_{12})$-heterocycloalkyl, —$(C_6-C_{20})$-aryl, or —$(C_3-C_{20})$-heteroaryl, may each independently be substituted by one or more substituents selected from —$(C_1-C_{12})$-alkyl, —O—$(C_1-C_{12})$-alkyl-$(C_6-C_{20})$-aryl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl.

In one embodiment, the $R^1$, $R^2$, $R^3$, $R^4$ radicals, if they are —$(C_1-C_{12})$-alkyl, —$(C_3-C_{12})$-cycloalkyl, —$(C_3-C_2)$-heterocycloalkyl, —$(C_6-C_{20})$-aryl, or —$(C_3-C_{20})$-heteroaryl, may each independently be substituted by one or more substituents selected from —$(C_1-C_{12})$-alkyl and —$(C_3-C_{20})$-heteroaryl.

In one embodiment, the $R^1$, $R^2$, $R^3$, $R^4$ radicals are unsubstituted if they are —$(C_1-C_{12})$-alkyl, —$(C_3-C_{12})$-cycloalkyl, or —$(C_3-C_{12})$-heterocycloalkyl, and may be substituted as described if they are —$(C_6-C_{20})$-aryl, or —$(C_3-C_{20})$-heteroaryl.

In one embodiment, the $R^1$, $R^2$, $R^3$, $R^4$ radicals are unsubstituted if they are —$(C_1-C_{12})$-alkyl, —$(C_3-C_{12})$-cycloalkyl, —$(C_3-C_{20})$-heterocycloalkyl, —$(C_6-C_{20})$-aryl, or —$(C_3-C_{20})$-heteroaryl.

In one embodiment, $R^1$, $R^2$, $R^3$, $R^4$ are each independently selected from —$(C_1-C_{12})$-alkyl, —$(C_6-C_{20})$-aryl, —$(C_3-C_{20})$-heteroaryl;

where at least one of the $R^1$, $R^2$, $R^3$, $R^4$ radicals is a —$(C_3-C_{20})$-heteroaryl radical;

and $R^1$, $R^2$, $R^3$, $R^4$, if they are —$(C_1-C_{12})$-alkyl, —$(C_6-C_{20})$-aryl or —$(C_3-C_{20})$-heteroaryl, may each independently be substituted by one or more of the above-described substituents.

In one embodiment, at least two of the $R^1$, $R^2$, $R^3$, $R^4$ radicals are a —$(C_3-C_{20})$-heteroaryl radical.

In one embodiment, the $R^1$ and $R^3$ radicals are each a —$(C_3-C_{20})$-heteroaryl radical and may each independently be substituted by one or more of the substituents described above. Preferably, $R^2$ and $R^4$ are independently selected from —$(C_1-C_{12})$-alkyl, —$(C_3-C_{12})$-cycloalkyl, —$(C_3-C_{12})$-heterocycloalkyl, —$(C_6-C_{20})$-aryl, more preferably from —$(C_1-C_{12})$-alkyl, —$(C_3-C_{12})$-cycloalkyl, —$(C_6-C_{20})$-aryl, most preferably from —$(C_1-C_{12})$-alkyl. $R^2$ and $R^4$ may independently be substituted by one or more of the above-described substituents.

In one embodiment, the $R^1$, $R^2$, $R^3$ and $R^4$ radicals are a —$(C_6-C_{20})$-heteroaryl radical and may each independently be substituted by one or more of the substituents described above.

In one embodiment, the $R^1$, $R^2$, $R^3$ and $R^4$ radicals, if they are a heteroaryl radical, are each independently selected from heteroaryl radicals having five to ten ring atoms, preferably five or six ring atoms.

In one embodiment, the $R^1$, $R^2$, $R^3$ and $R^4$ radicals, if they are a heteroaryl radical, are a heteroaryl radical having five ring atoms.

In one embodiment, the $R^1$, $R^2$, $R^3$ and $R^4$ radicals, if they are a heteroaryl radical, are each independently selected from heteroaryl radicals having six to ten ring atoms.

In one embodiment, the $R^1$, $R^2$, $R^3$ and $R^4$ radicals, if they are a heteroaryl radical, are a heteroaryl radical having six ring atoms.

In one embodiment, the $R^1$, $R^2$, $R^3$ and $R^4$ radicals, if they are a heteroaryl radical, are selected from furyl, thienyl, pyrrolyl, oxazolyl, isoxazolyl, thiazolyl, isothiazolyl, imidazolyl, pyrazolyl, furazanyl, tetrazolyl, pyridyl, pyridazinyl, pyrimidyl, pyrazinyl, benzofuranyl, indolyl, isoindolyl, benzimidazolyl, quinolyl, isoquinolyl, where the heteroaryl radicals mentioned may be substituted as described above.

In one embodiment, the $R^1$, $R^2$, $R^3$ and $R^4$ radicals, if they are a heteroaryl radical, are selected from furyl, thienyl, pyrrolyl, imidazolyl, pyridyl, pyrimidyl, indolyl, where the heteroaryl radicals mentioned may be substituted as described above.

In one embodiment, the $R^1$, $R^2$, $R^3$ and $R^4$ radicals, if they are a heteroaryl radical, are selected from 2-furyl, 2-thienyl, 2-pyrrolyl, 2-imidazolyl, 2-pyridyl, 2-pyrimidyl, 2-indolyl, where the heteroaryl radicals mentioned may be substituted as described above.

In one embodiment, the $R^1$, $R^2$, $R^3$ and $R^4$ radicals, if they are a heteroaryl radical, are selected from 2-furyl, 2-thienyl, N-methyl-2-pyrrolyl, N-phenyl-2-pyrrolyl, N-(2-methoxyphenyl)-2-pyrrolyl, 2-pyrrolyl, N-methyl-2-imidazolyl, 2-imidazolyl, 2-pyridyl, 2-pyrimidyl, N-phenyl-2-indolyl, 2-indolyl, where the heteroaryl radicals mentioned have no further substitution.

More preferably, the $R^1$, $R^2$, $R^3$ and $R^4$ radicals, if they are a heteroaryl radical, are pyridyl, especially 2-pyridyl.

In one embodiment, $R^1$ and $R^3$ are a pyridyl radical, preferably 2-pyridyl, and $R^2$ and $R^4$ are —$(C_1-C_{12})$-alkyl, where $R^1$, $R^2$, $R^3$ and $R^4$ may each be substituted as described above.

In one embodiment, the phosphine ligands are a compound of formula (1):

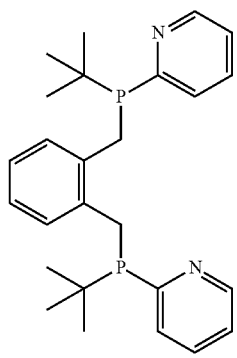

(1)

The alcohols used in step a) as a starting product in the process according to the invention comprise 2 to 30 carbon atoms, preferably 3 to 22 carbon atoms, more preferably 4 to 12 carbon atoms. They may be primary, secondary or tertiary alcohols. The alcohols may also comprise aromatic groups.

The alcohol used in step a) is preferably a secondary or tertiary alcohol.

In one embodiment, the first alcohol used in step a) is a compound of the formula (IV)

(IV)

where $R^5$ is selected from —$(C_1-C_{12})$-alkyl, —$(C_3-C_{12})$-cycloalkyl, —$(C_6-C_{20})$-aryl;

and $R^6$ and $R^7$ are each independently selected from —H, —$(C_1-C_{12})$-alkyl, —$(C_3-C_{12})$-cyclo-alkyl, —$(C_6-C_{20})$-aryl.

In one preferred embodiment, $R^5$ is —$(C_1-C_{12})$-alkyl. Preferably $R^5$ is selected from methyl, ethyl, n-propyl, 2-propyl, n-butyl, 2-butyl, sec-butyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl. More preferably $R^5$ is selected from methyl and ethyl. Most preferably $R^5$ is methyl.

In one preferred embodiment, $R^6$ and $R^7$ are each independently selected from —H, —$(C_1-C_{12})$-alkyl and —$(C_6-C_{20})$-aryl. Preferably $R^6$ and $R^7$ are each independently selected from —H, methyl, ethyl, n-propyl, 2-propyl, n-butyl, 2-butyl, sec-butyl, tert-butyl, n-pentyl, 2-pentyl, 3-pentyl, 2-methylbutyl, 3-methylbuty, 3-methylbut-2-yl, 2-methylbut-2-yl, 2,2-dimethylpropyl and phenyl.

More preferably $R^6$ and $R^7$ are each independently selected from —H, methyl, ethyl, n-propyl, 2-propyl, n-butyl, 2-butyl, sec-butyl, tert-butyl and phenyl.

Preferably not more than one of the radicals $R^6$ and $R^7$ is —H.

In one embodiment, $R^5$ is methyl and $R^6$ and $R^7$ are selected independently from —H, methyl, tert-butyl and phenyl, with not more than one of the radicals $R^6$ and $R^7$ being —H.

In an alternative embodiment, $R^6$ and $R^7$ are each independently selected from —$(C_1-C_{12})$-alkyl and —$(C_6-C_{20})$-aryl. Preferably $R^6$ and $R^7$ in this case are each independently selected from methyl, ethyl, n-propyl, 2-propyl, n-butyl, 2-butyl, sec-butyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl and phenyl.

More preferably $R^6$ and $R^7$ in this case are each independently selected from methyl, ethyl, n-propyl, 2-propyl, n-butyl, 2-butyl, sec-butyl, tert-butyl and phenyl. In this embodiment, in particular, $R^5$ may be methyl, and $R^6$ and $R^7$ are each independently selected from methyl, tert-butyl and phenyl.

In one preferred embodiment, the first alcohol is selected from tert-butanol, 3,3-dimethyl-butan-2-ol and 1-phenylethanol.

The alkoxycarbonylation according to the invention is catalysed by a Pd complex. The Pd complex may either be added in process step b) as a preformed complex comprising Pd and the phosphine ligands or be formed in situ from a compound comprising Pd and the free phosphine ligand. In this context, the compound comprising Pd is also referred to as catalyst precursor.

The preformed complexes may also comprise further ligands which coordinate to the metal atom. These are, for example, ethylenically unsaturated compounds or anions. Suitable additional ligands are, for example, styrene, acetate anions, maleimides (e.g. N-methyl-maleimide), 1,4-naphthoquinone, trifluoroacetate anions or chloride anions.

In the case that the catalyst is formed in situ, the ligand can be added in excess, such that the unbound ligand is also present in the reaction mixture.

In the case of the complex which is added right at the start as well, it is additionally possible to add further ligand, such that unbound ligand is also present in the reaction mixture.

In one variant, the compound comprising Pd is selected from palladium chloride ($PdCl_2$), palladium(II) acetylacetonate [$Pd(acac)_2$], palladium(II) acetate [$Pd(OAc)_2$], dichloro (1,5-cyclooctadiene) palladium(II) [$Pd(cod)_2Cl_2$], bis(dibenzylideneacetone)palladium [$Pd(dba)_2$], bis(acetonitrile)dichloropalladium(II) [$Pd(CH_3CN)_2Cl_2$], palladium(cinnamyl) dichloride [$Pd(cinnamyl)Cl_2$].

Preferably, the compound comprising Pd is $PdCl_2$, $Pd(acac)_2$ or $Pd(OAc)_2$. $Pd(acac)_2$ is particularly suitable.

The second alcohol in process step c) may be branched or linear, cyclic, alicyclic or partly cyclic, and is especially a $C_1$- to $C_{30}$-alkanol. It is possible to use monoalcohols or polyalcohols.

Preferably, the alcohol used in step c) is a primary alcohol.

The alcohol used is preferably an aliphatic alcohol. An aliphatic alcohol in the context of this invention refers to an alcohol which does not comprise any aromatic groups, i.e., for example, an alkanol, alkenol or alkynol. Therefore, unsaturated nonaromatic alcohols are also permitted.

The alcohol in process step c) comprises preferably 1 to 30 carbon atoms, more preferably 1 to 22 carbon atoms, especially preferably 1 to 12 carbon atoms. It may be a monoalcohol or a polyalcohol.

The alcohol may, in addition to the one or more hydroxyl groups, contain further functional groups. Preferably, the alcohol may additionally comprise one or more functional groups selected from carboxyl, thiocarboxyl, sulpho, sulphinyl, carboxylic anhydride, imide, carboxylic ester, sulphonic ester, carbamoyl, sulphamoyl, cyano, carbonyl, carbonothioyl, sulphhydryl, amino, ether, thioether, or silyl groups and/or halogen substituents.

In one embodiment, the alcohol does not comprise any further functional groups except for hydroxyl groups.

In one variant of the process, the alcohol in process step c) is selected from the group of the monoalcohols.

In one variant of the process, the alcohol in process step c) is selected from: methanol, ethanol, 1-propanol, 2-propanol, 1-butanol, 2-butanol, sec-butanol, tert-butanol, 1-pentanol, 2-pentanol, 3-pentanol, 1-hexanol, cyclohexanol, 2-ethylhexanol, isononanol, 2-propyl-heptanol, phenol, benzyl alcohol.

In a preferred variant, the alcohol in process step c) is selected from methanol, ethanol, 1-propanol, 1-butanol, 1-pentanol, 1-hexanol, 2-propanol, tert-butanol, 3-pentanol, cyclohexanol, and mixtures thereof.

In one variant of the process, the alcohol in process step c) is selected from the group of the polyalcohols.

In one variant of the process, the alcohol in process step c) is selected from: dials, trials, tetraols.

In one variant of the process, the alcohol in process step c) is selected from: cyclohexane-1,2-dial, ethane-1,2-diol, propane-1,3-diol, glycerol, butane-1,2,4-triol, 2-hydroxymethylpropane-1,3-diol, 1,2,6-trihydroxyhexane, pentaerythritol, 1,1,1-tri(hydroxyrnethyl)ethane, catechol, resorcinol and hydroxyhydroquinone.

In one variant of the process, the alcohol in process step c) is selected from: sucrose, fructose, mannose, sorbose, galactose and glucose.

In a preferred embodiment of the process, the alcohol in process step c) is selected from methanol, ethanol, 1-propanol, 1-butanol, 1-pentanol, 1-hexanol.

In a particularly preferred variant of the process, the alcohol in process step c) is selected from methanol and ethanol.

In a particularly preferred variant of the process, the alcohol in process step c) is methanol.

In one variant of the process, the alcohol in process step c) is used in excess.

In one variant of the process, the alcohol in process step c) is used simultaneously as solvent.

In one variant of the process, a further solvent is used, selected from: toluene, xylene, tetrahydrofuran (THF) and methylene chloride ($CH_2Cl_2$).

CO is fed in in step d) preferably at a partial CO pressure between 0.1 and 10 MPa (1 to 100 bar), preferably between 1 and 8 MPa (10 to 80 bar), more preferably between 2 and 4 MPa (20 to 40 bar).

The reaction mixture is heated in step e) of the process according to the invention preferably to a temperature between 10° C. and 180° C., preferably between 20 and 160° C., more preferably between 40 and 120° C., in order to convert the alcohol to an ester.

The molar ratio of the alcohol initially charged in step a) to the alcohol added in step c) is preferably between 1:1 and 1:20, more preferably 1:2 to 1:10, more preferably 1:3 to 1:4.

The mass ratio of Pd to the alcohol initially charged in step a) is preferably between 0.001% and 0.5% by weight, preferably between 0,01% and 0.1% by weight, more preferably between 0.01% and 0.05% by weight.

The molar ratio of the phosphine ligand to Pd is preferably between 0.1:1 and 400:1, preferably between 0.5:1 and 400:1, more preferably between 1:1 and 100:1, most preferably between 2:1 and 50:1.

Preferably, the process is conducted with addition of an acid. In one variant, the process therefore additionally comprises step c'): adding an acid to the reaction mixture. This may preferably be a Brøonsted or Lewis acid.

Suitable Brøensted acids preferably have an acid strength of $pK_a \le 5$, preferably an acid strength of $pK_a \le 3$. The reported acid strength $pK_a$ is based on the $pK_a$ determined under standard conditions (25° C., 1.01325 bar). In the case of a polyprotic acid, the acid strength $pK_a$ in the context of this invention relates to the $pK_a$ of the first protolysis step.

Preferably, the acid is not a carboxylic acid.

Suitable Brønsted acids are, for example, perchloric acid, sulphuric acid, phosphoric acid, methylphosphonic acid and sulphonic acids. Preferably, the acid is sulphuric acid or a sulphonic acid. Suitable sulphonic acids are, for example, methanesulphonic acid, trifluoromethanesulphonic acid, tert-butanesulphonic acid, p-toluenesulphonic acid (PTSA), 2-hydroxypropane-2-sulphonic acid, 2,4,6-trimethylbenzenesulphonic acid and dodecylsulphonic acid. Particularly preferred acids are sulphuric acid, methanesulphonic acid, trifluoromethanesulphonic acid and p-toluenesulphonic acid.

A Lewis acid used may, for example, be aluminium triflate.

In one embodiment, the amount of acid added in step c') is 0.3 to 40 mol %, preferably 0.4 to 15 mol %, more preferably 0.5 to 5 mol %, most preferably 0.6 to 4 mol %, based on the molar amount of the alcohol used in step a).

It is also possible for a molecular sieve to be added to the reaction mixture. In certain cases, this measure increases the yield of ester. Suitable for this purpose, for example, are molecular sieves comprising zeolite or comprising carbon, preferably molecular sieves comprising zeolite. The pore size of the molecular sieve is preferably in the range from 1 to 10 Å, more preferably in the range from 2 to 6 Å, most preferably in the range from 3 to 5 Å.

EXAMPLES

The examples which follow illustrate the invention.
General Procedures
All the preparations which follow were carried out under protective gas using standard Schlenk techniques. The solvents were dried over suitable desiccants before use (Purification of Laboratory Chemicals, W. L. F. Armarego (Author), Christina Chai (Author). Butterworth Heinemann (Elsevier), 6th edition, Oxford 2009).

Phosphorus trichloride (Aldrich) was distilled under argon before use. All preparative operations were effected in baked-out vessels. The products were characterized by means of NMR spectroscopy. Chemical shifts (δ) are reported in ppm. The $^{31}$P NMR signals were referenced as follows: $SR_{31p} = SR_{1H}*(BF_{31p}/BF_{1H}) = SR_{1H}*0.4048$. (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl. Chem., 2008, 80, 59-84).

The recording of nuclear resonance spectra was effected on Bruker Avance 300 or Bruker Avance 400, gas chromatography analysis on Agilent GC 7890A, elemental analysis on Leco TruSpec CHNS and Varian ICP-OES 715, and ESI-TOF mass spectrometry on Thermo Electron Finnigan MAT 95-XP and Agilent 6890 N/5973 instruments.

Preparation of chloro-2-pyridyl-tert-butylphosphine (Precursor A)

The Grignard for the synthesis of chloro-2-pyridyl-t-butylphosphine is prepared by the "Knochel method" with isopropylmagnesium chloride (Angew. Chem. 2004, 43, 2222-2226). The workup is effected according to the method of Budzelaar (Organometallics 1990, 9, 1222-1227).

Scheme 1: Synthesis of precursor A

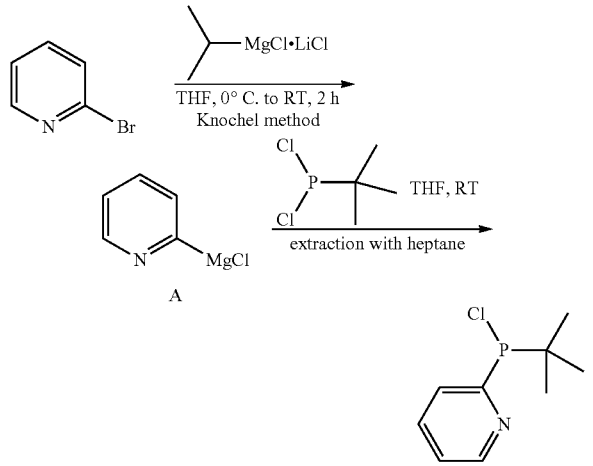

8.07 ml of a 1.3 M isopropylmagnesium chloride solution (Knochel's reagent) are introduced into a 50 ml round-bottom flask with magnetic stirrer and septum, and cooled to −15° C.

Thereafter, 953.5 μl (10 mmol) of 2-bromopyridine are rapidly added dropwise. The solution immediately turns yellow. It is allowed to warm up to −10° C. The conversion of the reaction is determined as follows: about 100 μl solution are taken and introduced into 1 ml of a saturated ammonium chloride solution. If the solution "bubbles", not much Grignard has formed yet. The aqueous solution is extracted with a pipette of ether and the organic phase is dried over $Na_2SO_4$. A GC of the ethereal solution is recorded. When a large amount of pyridine has formed compared to 2-bromopyridine, conversions are high. At −10° C., there has been little conversion. After warming up to room temperature and stirring for 1-2 hours, the reaction solution turns brown-yellow. A GC test shows complete conversion, Now the Grignard solution can be slowly added dropwise with a syringe pump to a solution of 1.748 g (11 mmol) of dichloro.tert-butylphosphine in 10 ml of THF which has been cooled to −15° C. beforehand. It is important that the dichloro-tert-butylphosphine solution is cooled. At room temperature, considerable amounts of dipyridyl-tert-butylphosphine would be obtained. A clear yellow solution is initially formed, which then turns cloudy. The mixture is left to warm up to room temperature and to stir overnight, According to GC-MS, a large amount of product has formed. The solvent is removed under high vacuum and a whitish solid which is brown in places is obtained. The solid is suspended with 20 ml of heptane and the solid is comminuted in an ultrasound bath. After allowing the white solid to settle out, the solution is decanted. The operation is repeated twice with 10-20 ml each time of heptane, After concentration of the heptane solution under high vacuum, it is distilled under reduced pressure. At 4.6 mbar, oil bath 120° C. and distillation temperature 98° C., the product can be distilled. 1.08 g of a colourless oil are obtained. (50%).

Analytical data: $^1$H NMR (300 MHz, $C_6D_6$): δ 8.36 (m, 1H, Py), 7.67 (m, 1H, Py), 7.03-6.93(m, 1H, Py), 6.55-6.46 (m, 1H, Py), 1.07 (d, J=13.3 Hz, 9H, t-Bu).

$^{13}$C NMR (75 MHz, $C_6D_6$): δ 162.9, 162.6, 148.8, 135.5, 125.8, 125.7, 122.8, 35.3, 34.8, 25.9 and 25.8.

$^{31}$P NMR (121 MHz, $C_6D_6$) δ 97.9.

MS (EI) m:z (relative intensity) 201 (M$^+$, 2), 147(32), 145 (100), 109 (17), 78 (8), 57.1 (17).

Preparation of Ligand 1 (α,α'-bis(2-pyridyl(t-butyl)phosphino)o-xylene)

Scheme 2: Synthesis of ligand 1

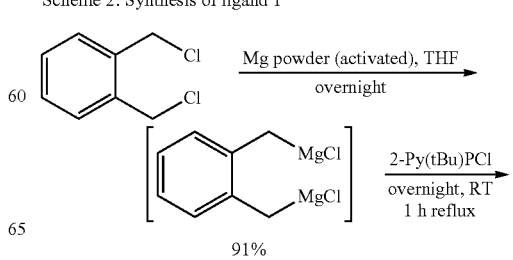

-continued

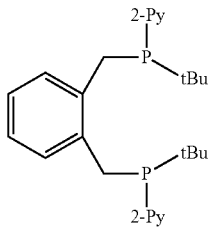

(Lit: Graham Eastham et al., U.S. Pat. No. 6,335,471)

675 mg (27.8 mmol, 4 eq) of Mg powder are weighed out in a glovebox in a 250 ml round-bottom flask with a nitrogen tap and magnetic stirrer bar, and the flask is sealed with a septum. High vacuum is applied to the round-bottom flask (about $5 \times 10^{-2}$ mbar) and it is heated to 90° C. for 45 minutes. After cooling down to room temperature, 2 grains of iodine are added and the mixture is dissolved in 20 ml of THF. The suspension is stirred for about 10 minutes until the yellow colour of the iodine has disappeared. After the magnesium powder has settled out, the cloudy THF solution is decanted and the activated magnesium powder is washed twice with 1-2 ml of THF. Then another 20 ml of fresh THF are added. At room temperature, a solution of 1.21 g (6.9 mmol) of α,α'-dichloro-o-xylene in 70 ml of THF is slowly added dropwise with a syringe pump. The THF solution gradually turns a darker colour. The next day, the THF suspension is filtered to remove the unconverted magnesium powder and the content of Grignard compound is determined as follows:

1 ml of Grignard solution is quenched in a saturated aqueous solution of $NH_4Cl$ and extracted with ether. After drying over $Na_2SO_4$, a GC of the ether solution is recorded. In qualitative terms, it is observed that exclusively o-xylene has formed.

Quantitative determination of the content of the Grignard solution:

1 ml of Grignard solution is quenched with 2 ml of 0.1 M HCl and the excess acid is titrated with 0.1 M NaOH. A suitable indicator is an aqueous 0,04% brornocresol solution. The colour change goes from yellow to blue. 0.74 ml of 0.1 M NaOH has been consumed. 2 ml−0.74 ml=1.26 ml, corresponding to 0.126 mmol of Grignard compound, Since a di-Grignard is present, the Grignard solution is 0.063 M. This is a yield exceeding 90%.

In a 250 ml three-neck flask with reflux condenser and magnetic stirrer, under argon, 1.8 g (8.66 mmol) of chlorophosphine (2-Py(tBu)PCl) are dissolved in 10 ml of THF and cooled to −60° C. Then 55 ml of the above-stipulated Grignard solution (0.063 M, 3.46 mmol) are slowly added dropwise at this temperature with a syringe pump. The solution at first remains clear and then turns intense yellow. After 1.5 hours, the solution turns cloudy. The mixture is left to warm up to room temperature overnight and a clear yellow solution is obtained. To complete the reaction, the mixture is heated under reflux for 1 hour. After cooling, 1 ml of $H_2O$ is added and the solution loses colour and turns milky white. After removing THF under high vacuum, a stringy, pale yellow solid is obtained. 10 ml of water and 10 ml of ether are added thereto, and two homogeneous clear phases are obtained, which have good separability. The aqueous phase is extracted twice with ether. After the organic phase has been dried with $Na_2SO_4$, the ether is removed under high vacuum and a stringy, almost colourless solid is obtained. The latter is dissolved in 5 ml of MeOH while heating on a water bath and filtered through Celite. At −28° C., 772 mg of product are obtained in the form of white crystals overnight. (51%), After concentration, it was possible to isolate another 100 mg from the mother solution. The overall yield is 57.6%.

$^1$H NMR (300 MHz, $C_6D_6$): δ 8.58 (m, 2H, Py), 7.31-7.30 (m, 2H, benzene), 7.30-7.22 (m, 2H, Py), 6.85-6.77 (m, 2H, Py), 6.73 (m, 2H, benzene), 6.57-6.50 (m, 2H, py), 4.33 (dd, J=13.3 and 4.3 Hz, 2H, $CH_2$), 3.72-3.62 (m, 2H, $CH_2$), 121(d, J=11.8 Hz, 18H, tBu), $^{13}$C NMR (75 MHz, $C_6D_6$): δ 161.3, 161.1, 149.6, 137.8, 137.7, 134.5, 133.3, 132.7, 131.4, 131.3, 125.7, 122.9, 30.7, 30.5, 28.2, 28.0, 26.5, 26.4, 26.2, and 26.1.

$^{31}$P NMR (121 MHz, $C_6D_6$) δ 8.8, EA calculated for $C_{26}H_{34}N_2P_2$; C, 71,54: H, 7.85; N, 6.56; P,14.35, found: C, 71.21; H, 7.55; N, 6.56; P, 14.35.

Comparative Ligand

The comparative ligand used in the following examples is 1,2-bis(di-tert-butylphosphino-methyl)benzene (DTBMB, ligand 3).

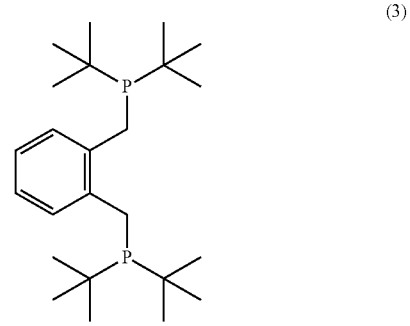 [SMILES: CC(C)(C)P(Cc1ccccc1CP(C(C)(C)C)C(C)(C)C)C(C)(C)C]

(3)

Methoxycarbonylation of tert-butanol

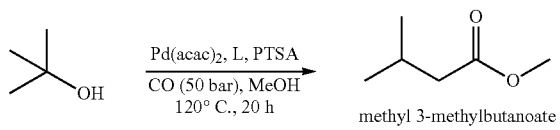

methyl 3-methylbutanoate

1) Without Ligand (Comparative Example)

A 4 ml glass reaction vessel (vial) is charged under argon with $Pd(acac)_2$ (3.1 mg, 0.5 mol %), PTSA (28.5 mg, 7.5 mol %) and a magnetic stirrer. Then, under argon, MeOH (2 ml) and tert-butanol (0.2 ml, 2 mmol) are added. This vial is placed in a metal plate fabricated for this purpose, and the plate with vial is transferred to a 300 ml autoclave from Parr Instruments. The autoclave is purged three times with CO and then charged with 50 bar of CO at room temperature. The reaction is carried out with magnetic stirring at 120° C. for 20 hours. After cooling down to room temperature, the autoclave is cautiously decompressed. The yield was carried out by means of GC analysis with isooctane (200 μl) as internal standard (0% yield of methyl 3-methylbutanoate).

2) Ligand 3 (Comparative Example)

A 4 ml glass reaction vessel (vial) is charged under argon with $Pd(acac)_2$ (3.1 mg, 0.5 mol %), 3 (15.8 mg, 2 mol %), PTSA (28.5 mg, 7.5 mol %) and a magnetic stirrer. Then, under argon, MeOH (2 ml) and tert-butanol (0.2 ml, 2 mmol) are added. This vial is placed in a metal plate fabricated for this purpose, and the plate with vial is transferred to a 300 ml autoclave from Parr Instruments. The autoclave is purged three times with CO and then charged with 50 bar of CO at room temperature. The reaction is carried out with magnetic stirring at 120° C. for 20 hours, After cooling down to room temperature, the autoclave is cautiously decompressed. The yield was carried out by means of GC analysis with isooctane (200 µl) as internal standard (0% yield of methyl 3-methylbutanoate).

3) Ligand 1

A 4 ml glass reaction vessel (vial) is charged under argon with Pd(acac)$_2$ (3.1 mg, 0.5 mol %), 1 (17.5 mg. 2 mol %), PTSA (28.5 mg. 7.5 mol %) and a magnetic stirrer. Then, under argon, MeOH (2 ml) and tert-butanol (0.2 ml, 2 mmol) are added. This vial is placed in a metal plate fabricated for this purpose, and the plate with vial is transferred to a 300 ml autoclave from Parr Instruments. The autoclave is purged three times with CO and then charged with 50 bar of CO at room temperature. The reaction is carried out with magnetic stirring at 120° C. for 20 hours, After cooling down to room temperature, the autoclave is cautiously decompressed. The yield was carried out by means of GC analysis with isooctane (200 µl) as internal standard (99% yield of methyl 3-methylbutanoate).

The results are summarized in the following table:

| Example | Ligand | Yield of methyl 3-methylbutanoate (%) |
|---------|--------|---------------------------------------|
| 1 (CE)  | none   | 0                                     |
| 2*      | 3      | 0                                     |
| 3 (CE)  | 1      | 99                                    |

CE: comparative example
*inventive example

Methoxycarbonylation of 1-phenylethanol

A 4 ml glass reaction vessel (vial) is charged under argon with Pd(acac)$_2$ (3.1 mg, 0.5 mol %), PTSA (28.5 mg, 7 mol %), ligand 1 (8.7 mg, 1 mol %) and a magnetic stirrer. Then, under argon, MeOH (2 ml) and 2 mmol of 1-phenylethanol are added. This vial is placed in a metal plate fabricated for this purpose, and the plate with vial is transferred to a 300 ml autoclave from Parr instruments. The autoclave is purged three times with CO and then charged with 50 bar of CO at room temperature. The reaction is carried out with magnetic stirring at 120° C. for 20 hours. After cooling down to room temperature, the autoclave is cautiously decompressed. The product obtained was a mixture of methyl 3-phenylpropanoate (n product) and methyl 2-phenylpropanoate (iso product). The yield was carried out by means of GC analysis with isooctane (200 µl) as internal standard (40% overall yield, n/iso ratio 70/30).

Methoxycarbonylation of 3,3-dimethylbutan-2-ol

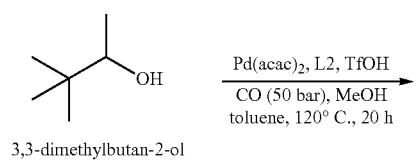

3,3-dimethylbutan-2-ol

Pd(acac)$_2$, L2, TfOH
CO (50 bar), MeOH
toluene, 120° C., 20 h

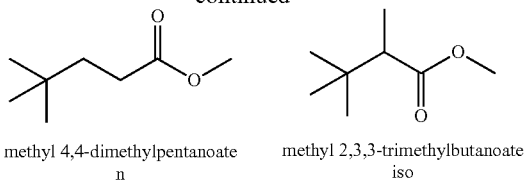

methyl 4,4-dimethylpentanoate
n methyl 2,3,3-trimethylbutanoate
iso

Example 1

Ligand 3

A 4 ml glass reaction vessel (vial) is charged under argon with Pd(acac)$_2$ (3.1 mg, 0.5 mol %), 3 (15.8 mg, 2 mol %), CF$_3$SO$_2$OH (48.0 mg, 16 mol %) and a magnetic stirrer. Then, under argon, toluene (2 ml) and 3,3-dimethylbutan-2-ol (0.25 ml, 2 mmol) are added. This vial is placed in a metal plate fabricated for this purpose, and the plate with vial is transferred to a 300 ml autoclave from Parr Instruments. The autoclave is purged three limes with CO and then charged with 50 bar of CO at room temperature. The reaction is carried out with magnetic stirring at 120° C. for 20 hours, After cooling down to room temperature, the autoclave is cautiously decompressed. The yield was carried out by means of GC analysis with isooctane (200 µl) as internal standard (0% yield).

Example 2

Ligand 3 with 4 Å Molecular Sieve

A 4 ml glass reaction vessel (vial) is charged under argon with Pd(acac)$_2$ (3.1 mg, 0.5 mol %), 3 (15.8 mg, 2 mol %), CF$_3$SO$_2$OH (48.0 mg, 16 mol %), 4 Å zeolite molecular sieve (4 Å MS, 20 mg) and a magnetic stirrer. Then, under argon, toluene (2 ml) and 3,3-dimethylbutan-2-ol (0.25 ml, 2 mmol) are added. This vial is placed in a metal plate fabricated for this purpose, and the plate with vial is transferred to a 300 ml autoclave from Parr Instruments. The autoclave is purged three times with CO and then charged with 50 bar of CO at room temperature. The reaction is carried out with magnetic stirring at 120° C. for 20 hours. After cooling down to room temperature, the autoclave is cautiously decompressed. The yield was carried out by means of GC analysis with isooctane (200 µl) as internal standard (0% yield).

Example 3

Ligand 1

A 4 ml glass reaction vessel (vial) is charged under argon with Pd(acac)$_2$ (3.1 mg, 0.5 mol %), 1 (17.5 mg, 2 mol %), CF$_3$SO$_2$OH (48.0 mg, 16 mol %) and a magnetic stirrer. Then, under argon, toluene (2 ml) and 3,3-dimethylbutan-2-ol (0.25 ml, 2 mmol) are added. This vial is placed in a metal plate fabricated for this purpose, and the plate with vial is transferred to a 300 ml autoclave from Parr Instruments. The autoclave is purged three times with CO and then charged with 50 bar of CO at room temperature. The reaction is carried out with magnetic stirring at 120° C. for 20 hours. After cooling down to room temperature, the autoclave is cautiously decompressed. The yield was carried out by means of GC analysis with isooctane (200 µl) as internal standard (10% yield).

Example 4

Ligand 1 with 4 Å Molecular Sieve

A 4 ml glass reaction vessel (vial) is charged under argon with Pd(acac)$_2$ (3.1 mg, 0.5 mol %), 1 (17.5 mg, 2 mol %), CF$_3$SO$_2$OH (48.0 mg, 16 mol %), 4 Å MS (20 mg) and a magnetic stirrer. Then, under argon, toluene (2 ml) and 3,3-dimethylbutan-2-ol (0.25 ml, 2 mmol) are added. This vial is placed in a metal plate fabricated for this purpose, and the plate with vial is transferred to a 300 ml autoclave from Parr Instruments. The autoclave is purged three times with CO and then charged with 50 bar of CO at room temperature. The reaction is carried out with magnetic stirring at 120° C. for 20 hours. After cooling down to room temperature, the autoclave is cautiously decompressed. The yield was carried out by means of GC analysis with isooctane (200 µl) as internal standard (20% yield).

The results are summarized in the following table:

| Example | Ligand | Additive | Yield | n/iso ratio |
|---------|--------|----------|-------|-------------|
| 1 (CE)  | 3      |          | 0%    | —           |
| 2 (CE)  | 3      | 4 Å MS   | 0%    | —           |
| 3*      | 1      |          | 10%   | 75/25       |
| 4*      | 1      | 4 Å MS   | 20%   | 74/26       |

CE: comparative examples
*inventive examples

The above experiments show that by means of the process of the invention, using the ligands according to the invention, a series of structurally different alcohols can be reacted as substrate in an alkoxycarbonylation reaction with CO and a further alcohol to form esters, Conversely, the ligand known from the prior art is not suitable for the reaction of alcohols in an alkoxycarbonylation reaction.

The invention claimed is:

1. A process for forming an ester mixture product having n- and iso-ester components from a corresponding first alcohol substrate and CO and a second alcohol comprising the following process steps:
   a) introducing the first alcohol selected from a secondary or tertiary alcohol, having 2 to 30 carbon atoms, to form a reaction mixture;
   b) adding a phosphine ligand and a compound which comprises Pd, or adding a complex comprising Pd and the phosphine ligand;
   c) adding the second alcohol;
   d) supplying CO;
   e) heating the reaction mixture, the first alcohol reacting with CO and then the second alcohol to form the ester mixture with the iso- and n-products;
   where the phosphine ligand is a compound of formula (I)

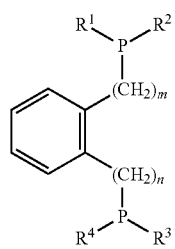

(I)

where m and n are each independently 0 or 1;
R$^1$, R$^2$, R$^3$, R$^4$ are each independently selected from —(C$_1$-C$_{12}$)-alkyl, —(C$_3$-C$_{12}$)-cycloalkyl, —(C$_3$-C$_{12}$)-heterocycloalkyl, —(C$_6$-C$_{20}$)-aryl or —(C$_3$-C$_{20}$)-heteroaryl, where each is substituted or unsubstituted; and at least one of the R$^1$, R$^2$, R$^3$, R$^4$ radicals is a —(C$_3$-C$_{20}$)-heteroaryl radical; wherein
the substituents are selected from
—(C$_1$-C$_{12}$)-alkyl, —(C$_3$-C$_{12}$)-cycloalkyl, —(C$_3$-C$_{12}$)-heterocycloalkyl, —O—(C$_1$-C$_{12}$)-alkyl, —O—(C$_1$-C$_{12}$)-alkyl-(C$_6$-C$_{20}$)-aryl, —O—(C$_3$-C$_{12}$)-cycloalkyl, —S—(C$_1$-C$_{12}$)-alkyl, —S—(C$_3$-C$_{12}$)-cycloalkyl, —COO—(C$_1$-C$_{12}$)-alkyl, —COO—(C$_3$-C$_{12}$)-cycloalkyl, —CONH—(C$_1$-C$_{12}$)-alkyl, —CONH—(C$_3$-C$_{12}$)-cycloalkyl, —CO—(C$_1$-C$_{12}$)-alkyl, —CO—(C$_3$-C$_{12}$)-cycloalkyl, —N—[(C$_1$-C$_{12}$)-alkyl]$_2$, —(C$_6$-C$_{20}$)-aryl, —(C$_6$-C$_{20}$)-aryl-(C$_1$-C$_{12}$)-alkyl, —(C$_6$-C$_{20}$)-aryl-O—(C$_1$-C$_{12}$)-alkyl, —(C$_3$-C$_{20}$)-heteroaryl, —(C$_3$-C$_{20}$)-heteroaryl-(C$_1$-C$_{12}$)-alkyl, —(C$_3$-C$_{20}$)-heteroaryl-O—(C$_1$-C$_{12}$)-alkyl, —COOH, —OH, —SO$_3$H, —NH$_2$ or halogen.

2. The process according to claim 1, where the phosphine ligand is a compound of one of the formulae (II) and (III)

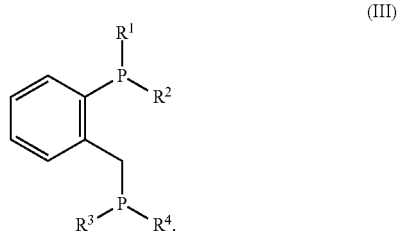

3. The process according to claim 1, where at least two of the R$^1$, R$^2$, R$^3$, R$^4$ radicals are a —(C$_3$-C$_{20}$)-heteroaryl radical.

4. The process according to claim 1,
where the R$^1$ and R$^3$ radicals are each a —(C$_3$-C$_{20}$)-heteroaryl radical.

5. The process according to claim 1,
where the R$^1$ and R$^3$ radicals are each a —(C$_3$-C$_{20}$)-heteroaryl radical;
and R$^2$ and R$^4$ are each independently selected from —(C$_1$-C$_{12}$)-alkyl, —(C$_3$-C$_{12}$)-cycloalkyl, —(C$_3$-C$_{12}$)-heterocycloalkyl or —(C$_6$-C$_{20}$)-aryl.

6. The process according to claim 1,
where the R$^1$ and R$^3$ radicals are each a —(C$_3$-C$_{20}$)-heteroaryl radical;
and R$^2$ and R$^4$ are each independently selected from —(C$_1$-C$_{12}$)-alkyl.

7. The process according to claim 1,
where R$^1$, R$^2$, R$^3$, R$^4$, if they are a heteroaryl radical, are each independently selected from furyl, thienyl, pyrrolyl, oxazolyl, isoxazolyl, thiazolyl, isothiazolyl, imidazolyl, pyrazolyl, furazolyl, tetrazolyl, pyridyl, pyridazinyl, pyrimidyl, pyrazinyl, benzofuranyl, indolyl, isoindolyl, benzimidazolyl, quinolyl or isoquinolyl.

8. The process according to claim 1,
wherein the first alcohol in process step a) is a compound of formula (IV)

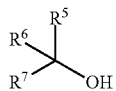
(IV)

where $R^5$ is selected from —($C_1$-$C_{12}$)-alkyl, —($C_3$-$C_{12}$)-cycloalkyl or —($C_6$-$C_{20}$)-aryl;
and $R^6$ and $R^7$ are each independently selected from —H, —($C_1$-$C_{12}$)-alkyl, —($C_3$-$C_{12}$)-cycloalkyl or —($C_6$-$C_{20}$)-aryl and wherein not more than one of the radicals $R^6$ and $R^7$.

9. The process according to claim 8,
wherein $R^5$ is —($C_1$-$C_{12}$)-alkyl.

10. The process according to claim 8,
where $R^6$ and $R^7$ are each independently selected from —H, —($C_1$-$C_{12}$)-alkyl or —($C_6$-$C_{20}$)-aryl.

11. The process according to claim 1,
wherein the compound comprising Pd in process step b) is selected from palladium dichloride, palladium(II) acetylacetonate, palladium(II) acetate, dichloro(1,5-cyclooctadiene)palladium(II), bis(dibenzylideneacetone)palladium, bis(acetonitrile)dichloropalladium(II) or palladium(cinnamyl) dichloride.

12. The process according to claim 1,
wherein the second alcohol in process step c) is selected from the group consisting of methanol, ethanol, 1-propanol, 1-butanol, 1-pentanol, 1-hexanol, 2-propanol, tert-butanol, 3-pentanol, cyclohexanol, and mixtures thereof.

13. The process according to claim 1,
wherein the second alcohol in process step c) is a primary alcohol.

14. A process for forming an ester mixture product having n- and iso-ester components from a corresponding first alcohol substrate and CO and a second alcohol comprising the following process steps:
a) introducing the first alcohol selected from a secondary or tertiary alcohol, having 2 to 30 carbon atoms, to form a reaction mixture;
b) adding a phosphine ligand and a compound which comprises Pd, or adding a complex comprising Pd and the phosphine ligand;
c) adding the second alcohol;
d) supplying CO;
e) heating the reaction mixture, the first alcohol reacting with CO and then the second alcohol to form the ester mixture with the iso- and n-products;
where the phosphine ligand is a compound of formula (1)

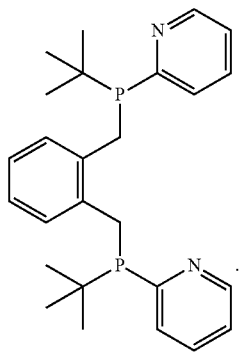
(1)

15. A process for forming an ester mixture product having n- and iso-ester components from a corresponding first alcohol substrate and CO and a second alcohol comprising the following process steps:
a) introducing the first alcohol selected from a secondary or tertiary alcohol, having 2 to 30 carbon atoms, to form a reaction mixture;
b) adding a phosphine ligand and a compound which comprises Pd, or adding a complex comprising Pd and the phosphine ligand;
c) adding the second alcohol;
d) supplying CO;
e) heating the reaction mixture, the first alcohol reacting with CO and then the second alcohol to form the ester mixture with the iso- and n-products; where the phosphine ligand is (α, α'-bis(2-pyridyl)(t-butyl)phosphino) o-xylene and the first alcohol is 3,3-dimethylbutan-2-ol.

* * * * *